United States Patent [19]
Whitcomb

[11] Patent Number: 6,156,743
[45] Date of Patent: Dec. 5, 2000

[54] METHOD OF DECREASING FATIGUE

[76] Inventor: John E. Whitcomb, 2095 Elm Tree Ct., Elm Grove, Wis. 53122

[21] Appl. No.: 09/420,118

[22] Filed: Oct. 18, 1999

[51] Int. Cl.$^7$ .................................................. A61K 31/573
[52] U.S. Cl. ............................................................ 514/179
[58] Field of Search ............................................. 514/179

[56] References Cited

PUBLICATIONS

McKenzie et al., JAMA, 280/20, 1061–66, Sep. 1998.
J.F. Waeckerle, "Circadian Rhythm, Shift Work and Emergency Physicians," Ann. Emerg. Med., (24) p. 959–961, (1994).
D.J. Skene, et al., "Use of Melatonin in Circadian Rhythm Disorders and Following Phase Shifts," Acta Neurobiol. Exp., (56) p. 359–36, (1996).
M. James, et al., "Can Melatonin Improve Adaptation to Night Shift?," Am. J. Emerg. Med., (6) p. 367–370, (1998).
S.W. Wright, et al., "Randomized Clinical Trial of Melatonin After Night–Shift Work: Efficacy an Neuropsycologic Effects," Ann. Emerg. Med., (3:3), p. 334–340, (1998).
M.M. Mitler, et al., "Catastrophes, Sleep, and Public Policy: Consensus Report," Sleep, (11:1), p. 100–109, (1988).
E.F. Mellor, "Shift work and flexitime: how prevalent are they?," Mon. Labor Rev., p. 14–21, (Nov. 1986).
F.G. Benedict, "Studies in Body–Temperature.—I. Influence of the Inversion of the Daily Routine; the Temperature of Night–Workers," Am. J. Physiolo., (1904), p. 145–169 (Admitted Prior Art).
P. Knauth, et al., "Experimental Shift Work Studies of Permanent Night, and Rapidly Rotating, Shift Systems," Int. Arch. Occup. Environ. Health, (46) p. 111–15, (1980).
S. Folklard, et al., "Short and Long–term Adjustment of Circadian Rhythms in 'Permanent:' Night Nurses," Ergonomics, vol. 21 (10) p. 785–799, (1978).
William Harris, "Fatigue, Circadian Rhythm, and Truck Accidents," Vigilance: Theory, Operational Performance, and Physiological Correlates, Plenum (New York), p. 133–146, (1977).
J. Foret, G. Lantin, "The Sleep of Train Drivers: An Example of the Effects of Irregular Work Schedules on Sleep," Aspect of Human Efficiency Serial Rhythm, p. 273–282, (1970).
C.A. Czeisler, et al., "Exposure to Bright Light and Darkness to Treat Physiologic Maladaptation to Night Work," N. Engl. J. Med., (32:18) p. 1253–1259, (1990).

M.C. Moore–Ede, et al., "Cortisol–mediated synchronization of circadian rhythm in urinary potassium excretion," Am. J. Physiol., p. 230–38, (1977).
M.C. Moore–Ede and G.S. Richardson, "Medical Implications of Shift–Work," Am Rev. Med., (36) p. 607–617, (1985).
J. Aschoff, "Circadian Rhythms Within and Outside Their Ranges of Entrainment," Environmental Endocrinology, Springer–Verlag (New York), p. 172–181, (1978).
K.L. Keller and W.J. Koenig, "Management of Stress and Prevention of Burnout in Emergency Physicians," Ann. Emerg. Med., (18:1) p. 42–47, (1989).
S.L. Adams, et al., "Ambulatory Blood Pressure and Holter Monitoring of Emergency Physicians before, during and after a Night Shift," Acad. Emerg. Med., (5:9) p. 871–877, (1998).
R. Smith–Coggins, et al., "Rotating Shiftwork Schedules: Can We Enhance Physician Adaptation to Night Shifts?," Acad. Emerg. Med., (4:9) p. 951–961, (1977).
H.E. Michaels, "Night Shift Work," Ann. Emerg. Med., (13:3), p. 201–202, (Mar. 1984).
E.J. Bartle, et al., "The effects of acute sleep deprivation during residency training," Surgery, (104) p. 311–316, (1988).
H. Raff and J.W. Findling, "A New Immunoradiometric Assay for Corticotropin Evaluated in Normal Subjects and Patients with Cushing's Syndrome," Clin. Chem., (35:4) p. 596–600, (1989).
A. Munck, et al., "Physiological Functions of Glucocorticoids in Stress and Their Relation to Pharmacological Actions," Endocrine Reviews, (5:1) p. 25–44, (1984).
E.R. De Kloet, "Brain Corticosteriod Receptor Balance and Homeostatic Control," Frontiers in Neuroendocrinology, Raven Press, Ltd. (New York), (1:2) p. 95–164, (1991).

*Primary Examiner*—Phyllis G. Spivack
*Attorney, Agent, or Firm*—Neil E. Hamilton

[57] ABSTRACT

A method of decreasing fatigue in humans who are shifting their time of wakefulness by administering an effective amount of hydrocortisone. The treatment is useful for those persons who must make an adjustment between their work hours and their usual sleep time such as night shift workers and those experiencing problems with jet lag.

10 Claims, 1 Drawing Sheet

METHOD OF DECREASING FATIGUE

BACKGROUND OF THE INVENTION

This invention relates to a method of decreasing fatigue in humans who switch their circadian rhythm reference times. More particularly, the invention is concerned with reducing fatigue in a human by administering hydrocortisone.

In the following description, certain references are mentioned. These are described at the end of the specification.

The need to be alert and competent on night duty in a profession that requires episodic night shifts is a major issue among emergency physicians, as with many professions in the modern industrial age[1]. Emergency physicians report substantial career dissatisfaction because of the burden of dealing with night shifts and the accompanying sleep disturbances[2]. Administration of hydrocortisone has not been used to decrease the perception of stress and improve mood during night shifts whereas melatonin has been evaluated as an endocrine intervention with variable findings[3,4,5].

The literature demonstrates greater accident rates on night shifts[6]. Physicians could be prone to that same tendency to error. The need to be alert, awake and competent, regardless of work shift is important to the customer of the night worker, just as the fatigue of the job is important to the worker.

To date, no studies exist in which hydrocortisone has been used as a means of assisting in the "phase shift". There are many descriptive studies on the circadian rhythms of shift workers, of airline stewardesses and others exposed to alterations in the normal human day-night cycle, either shift or meridian change suggesting that there is a good deal of fatigue and stress involved.

The fatigue of night duty has been clearly documented in the medical literature. Approximately 7.3 million American workers have night duty as part of their jobs[7] and rarely make a complete adaptation to night duty and day sleep [8,9,10]. As an expected consequence, work related accidents are far more frequent on the night shift[11,12]. The U.S. Dept. of Transportation reports that up to 200,000 traffic accidents each year may be sleep related and that 20% of all drivers have dozed off at least once while behind the wheel[13]. Though causes of major industrial accidents are always complex, it should be noted that Three Mile Island, Bhopal, Exxon Valdez and Chernobyl all occurred on the night shift. These events only raise the importance of addressing the issue of human adaptation to night duty as society emerges from a diurnal work place to the 24-hour industrial age.

Czeisler and Johnson reported on a physiologic method of adapting to night work[14], though their method required at least 4 days before physiologic adaptation occurred. They used bright lights during the night and complete dark during the day. This demonstrated that it takes time to adapt even with an efficient and carefully orchestrated protocol. This study did not address the need of managing the episodic single night which is the reality for many industrial age workers.

Moore-Ede and Schmelzer demonstrated in squirrel monkeys that cortisol mediates the synchronization of circadian rhythms[15]. Czeisler has shown that cortisol levels are at their nadir during the night hours, that cognitive performance and alertness decline during the progression of night hours to a nadir at 4–8 hours after midnight.

The effects of poor performance are not just transient. Moore-Ede has proposed the concept of a "shift maladaption" syndrome to describe the clinical pathologies observed in long time shift workers[16]. The consequences of repeated shift work over years have been poorly documented but include sleep-wake disorders, gastrointestinal pathology, and an increased risk of cardiovascular disorders[17]. Moore-Ede notes the extraordinary difficulty in studying night workers as they tend to be young, with few medical problems by merit of age. They tend to shift to day jobs as they gain seniority which invalidates longitudinal studies. Moore-Ede notes that the problems of jet leg, the physiological equivalent of shift work, are short term[17].

The ability of humans to adapt to a shift in circadian systems is limited. It can only be reset by a few hours a day and therefore has a limited "range of entrainment"[18]. The typical range of entrainment is approximately 23.5 to 26.5 hours for the synchronized human system, allowing a "phase advance" of 0.5 hours per day or a "phase delay" of 2.5 hours per day[11].

To date, no good research exists as to the length of the "average career length" of emergency physicians because the field is new. Experts in the field suggest lengths of 9–12 years prior to "burnout" and movement into other fields of medicine[17,19]. The need for Emergency Physician to remain alert and functionally competent is self-evident[20,21]. The correlation between the stress of nights and the longevity of career is also obvious[22].

It is therefore an object of the invention to provide a method of decreasing fatigue in humans.

It is also an object of the invention to provide a method of alleviating the effects of jet lag.

BRIEF SUMMARY OF THE INVENTION

The shortcomings of the prior art are overcome and the foregoing objects are accomplished in one aspect by decreasing fatigue in a human wherein hydrocortisone is administered to the human in an effective amount.

In another aspect, the hydrocortisone is administered at a dosage in the range of 20–40 mg.

In yet another aspect, the hydrocortisone is administered 1–2 hours prior to a predetermined time.

In still another aspect, hydrocortisone is administered in a single dose.

In yet another aspect, the fatigue of jet lag is reduced by administering to a human an effective amount of hydrocortisone on arrival at a destination.

In yet another aspect, the fatigue of jet lag is reduced by administering hydrocortisone at the precise time in the human circadian rhythm that correlates to the number of time zones changed and how these changes compare to the old reference time zones.

DETAILED DESCRIPTION OF THE INVENTION

Figure 1:
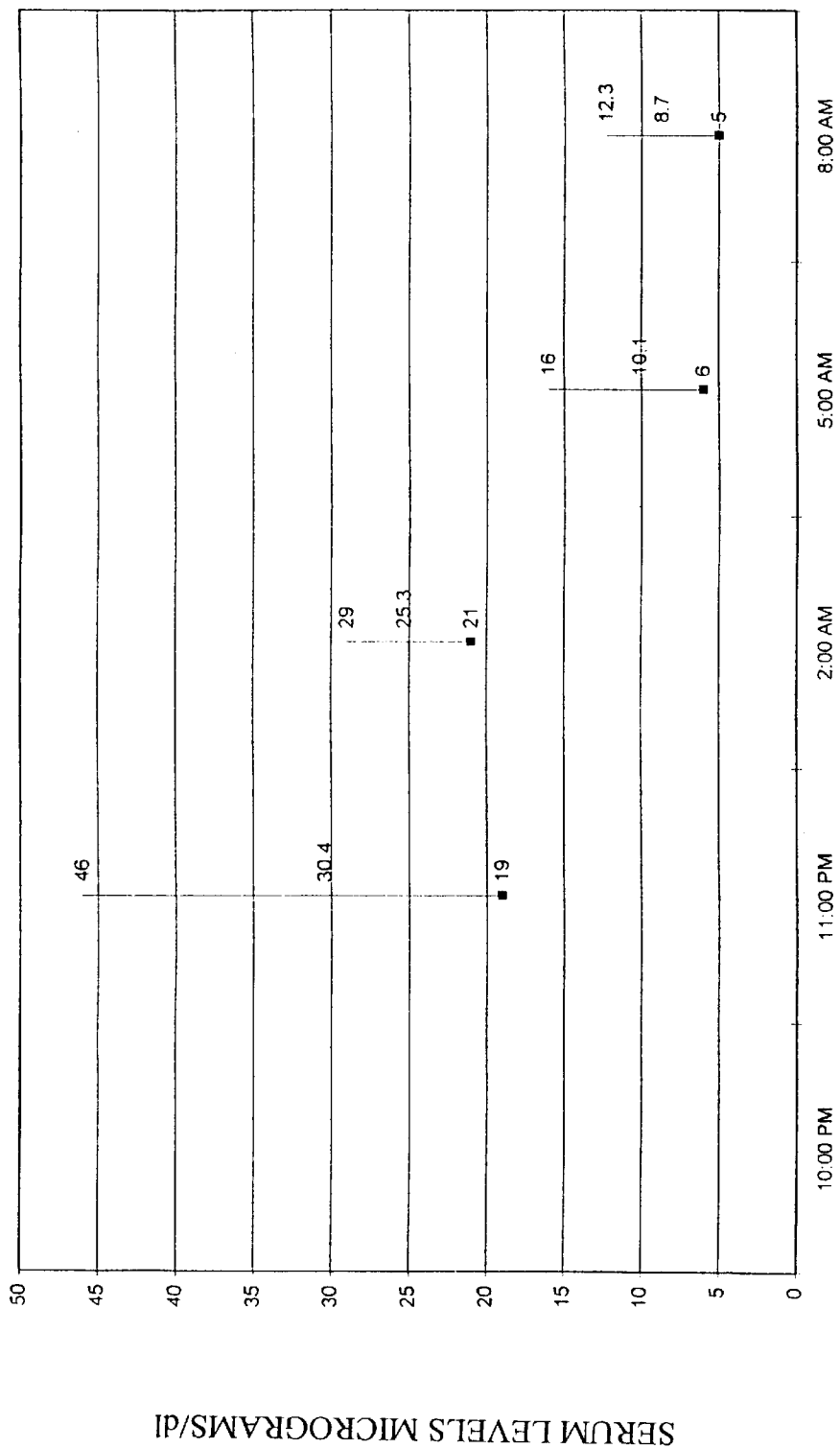
FIG. 1 is a chart showing serum hydrocortisone levels.

A study was conducted to mimic normal awakening (8 am) plasma cortisol levels at the start of a night shift. Psychological testing, subjective fatigue measures, and plasma ACTH and cortisol concentration were assessed. The hypothesis was that this intervention would decrease subjective fatigue, improve objective physiologic testing, and recreate a daytime endocrine profile of cortisol levels.

Materials and Methods

This was designed as a prospective, double-blind, placebo controlled, crossover trial of hydrocortisone given to practicing emergency physicians at the beginning of an episodic "first night" shift.

Subjects and Setting

Four male emergency physicians, ages 35–38, were recruited. Each subject was free of medical or psychiatric disorders including high blood pressure, diabetes or peptic ulcer disease or any medical illness requiring therapy. All were practicing actively on a full time basis, working 2–6 night shifts (8–10 hours each) and 30–40 hours a week of clinical time. All worked in busy urban emergency departments with more 30,000 patients a year. All study night shifts were isolated from previous night shifts by at least 10 days to allow for day entrainment. The study protocol was reviewed and approved by the Institutional Research Board.

Only "first nights" qualified as research nights. To be a first night necessitated 6 full days of prior day or evening work. Most patterns of night work involved 2–4 consecutive nights and then off night duty for several weeks. No restrictions were placed on activities or sleep prior to work.

The protocol for study nights was designed to avoid interruption of patient care. If the physician could not take the time off from patient care (10–12 minutes) to administer the testing protocols, the night was canceled as a study night.

A. Procedures.

Pretesting included a standard cosyntropin stimulation test (0.25 mg. of Cortrosyn, Organon) was injected IV between 8–10 am, with plasma samples for ACTH and cortisol collected before and 30 minutes after injection. This was performed to insure that all participants had a normal adrenal axis, and could then be compared to a post study test to insure no adverse effect of drug treatment. All participants also had a prestudy session in which they performed the standardized psychological tests chosen to assess mental alertness and competence[23]. These included the 60-second Peg Board[23] dexterity test, the Paced Auditory Serial Addition Test (PASAT)[23], the 60 second Digit Symbol Recognition[23] test and a Profile of Mood States[24].

A recorded audio tape was played that allowed for self-testing in a standardized time frame. The Peg Board Test has the subject use their dominant hand to place pegs from a basin to a board. The PASAT has numbers read in sequence between 1 and 10 with the subject required to add and write down the sum of the previous two numbers. The Digit Symbol Recognition test requires a standard set of symbols to be matched with numbers. The Profile of Mood States scale was designed to address fatigue and stress. It was completed last without time constraints.

The psychological tests were performed in response to an eight minute recorded tape with instructions and timed intervals on the tape. All subjects had identical times for each test and could administer their own testing with a witness to verify compliance.

A diary was designed to detail the subjective and objective features of the duty period. It assessed time since last night shift, amount of sleep obtained prior to coming to work, quality of sleep prior to work, number of patients seen on the shift in question, amount of caffeine consumed, amount of food eaten, subjective stress symptoms experienced during the shift (headache, GI upset, cold shivers etc.), and a judgment as to the quality of the shift in regards to stress and fatigue. (i.e. "Was it a good night?")

Four physicians were instructed to consume a gelatin capsule between 10 and 11 p.m. It contained either lactose as placebo or 40 mg of generic hydrocortisone. All capsules were prepared by the hospital pharmacy and coded to insure that only the pharmacist knew the content of the capsule. Each physician was given 5 nights of lactose and 5 nights of hydrocortisone in double-blinded randomized order. The physicians picked their own capsule from their assigned stock of envelopes and recorded the number on their diary. Extra nights were scheduled because of the need to cancel nights for busy shifts.

At approximately 1 hour and again at 5–6 hours after consumption of the study capsule, the physicians were instructed to take the battery of psychological tests and to have their blood drawn. If their work shift was quiet, sleep was permitted only after the second testing period. Emphasis was placed on patient care as the principle priority while on duty with performance of the study protocol dependent on time availability. A nurse on the night duty shift witnessed compliance with the time standards on the tape.

Plasma ACTH was measured by 2-site radioimmunometric assay[25]. Plasma cortisol was measured by radioimmunoassay (Diagnostic Products.)

Results

Complete data was collected during forty-two nights. Five nights were not included because physicians were too busy with patient care. Three potential study nights were not used for a variety of other reasons.

Subjective Data.

A subjective assessment of fatigue during the night showed that the physicians felt less fatigue on nights when they took hydrocortisone ($p<0.001$). This is shown in the following Table 1.

TABLE 1

Physician Perception of Fatigue of Night Shift With and Without Cortisol ($p < .001$)

| Question: | Did you have a good night | Hydrocortisone Given (n = 21) | Placebo (n = 21) |
|---|---|---|---|
| | Number Yes | 17 | 6 |
| | Number No | 4 | 15 |
| | Percent Yes | 81% | 29% |
| | 95% Confidence Interval | (63%–99%) | (8%–40%) |
| | | $p < .001$ | |

Of twenty-one (21) nights on which hydrocortisone was administered, seventeen (17) were identified as being "Good nights". Fifteen (15) of twenty-one (21) nights in which placebo was administered were considered "Bad".

Objective Psychological Data.

None of the objective psychological tests showed significant effects of hydrocortisone. The PASAT had a mean score of 51.3 at 11 p.m. to 51.7 at 5 am on placebo (of a possible 60). On hydrocortisone, it was 53.3 at 11 p.m. to 52.9 at 5 am. (p=NS) The Digit Symbol Recognition and Peg board tests also showed no significant change for nights in which hydrocortisone was used as opposed to placebo nights.

Answers to the questions regarding tension, depression, anger, showed that fatigue increased and vigor and clear-headedness.

No effect could be attributable to hydrocortisone use on any of the neuropsychiatric tasks ($p>0.50$ for the PASAT and Digit Symbol: $p>0.10$ for pegboard). On the other hand, pre-shift performance was found to be a significant determinant of post-shift performance regardless of drug use ($p=0.001$).

FIG. I shows plasma cortisol measured at 11 p.m., 2 am, 5 am and 8 am after the oral dose of hydrocortisone was given at 10 p.m. Plasma cortisol levels peaked shortly after the oral dose and then declined over 9 hours.

Table 2 shows the levels of plasma ACTH and plasma cortisol on the subjects on placebo and hydrocortisone.

Plasma levels of cortisol in male subjects after 40 mg. oral dose at 10 p.m. (μg/dl) performed while daylight entrained (at least 6 days since working a night shift.

TABLE 2

Plasma Levels of Cortisol and ACTH at 11 p.m. and 5 a.m.

|  | Cortisol in μm/dl | | ACTH in pg/ml | |
| --- | --- | --- | --- | --- |
|  | 11 p.m. | 5 a.m. | 11 p.m. | 5 a.m. |
| Placebo night | 4.9 ± 1.8<br>N = 4 | 12.1 ± 3.4<br>N = 4 | 20.9 ± 7.8<br>N = 4 | 37.4 ± 11.1<br>N = 4 |
| Hydrocortisone night | 34.9 ± 11.8<br>N = 4 | 8.9 ± 1.7<br>N = 4 | 15.6 ± 7.0<br>N = 3 | 10.5 ± 3.5<br>N = 4 |

A late p.m. dose of 40 mg. of hydrocortisone dose appeared to slightly suppress the 5 a.m. rise in plasma cortisol that was observed on placebo nights. With an N of four, this did not reach statistical significance.

Cosyntropin stimulation tests were normal and not different before and after completion of the study.

Physicians indicated more adverse subjective symptoms on night shifts without cortisol versus night shifts with cortisol. With such a small number of participants, significance could not be ascertained. A total of 8 comments were registered for adverse symptoms such as headache, GI distress, and feeling cold on placebo nights verses 5 such symptoms on cortisol nights.

Statistical Methods

Plasma cortisol and ACTH level were compared by use of analysis of variance, with the 11 p.m. to 5 am treated as a repeated measure. Categorical data was tested for significance by use of the chi-square test.

The study demonstrated that the subjective sense of fatigue felt by night workers can be reduced by the administration of hydrocortisone. Objective testing was not measurably different on standardized neuropsychological tests.

This study is the first in the literature to intervene on night shifts with a "missing ingredient". Cortisol is a hormone responsible for supporting diurnal metabolic cycles. The first night shift of a day-entrained person is relatively cortisol deficient. It could be argued that supplying the missing cortisol by administering hydrocortisone is an important adjunct for the night shift worker. This has not yet been explored by any further study and remains conjecture.

Although this study did not address the mechanisms by which hydrocortisone replacement might improve function, there are several possibilities. The first is that administration of hydrocortisone at its normal circadian nadir might increase glucose and other substrate supply thereby minimizing fatigue[26]. Another more likely possibility is that increasing plasma cortisol improves mood and perception of function by a direct action on the brain and, in particular, the limbic system[27].

The objective performance data indicated that there was no difference on neuro-psychological testing between cortisol nights and placebo nights. This corroborated the literature on surgery residents done in the late 1980[23]. It is the routine and the mundane that are markedly difficult to maintain. Testing by itself is a challenge that forces alertness, making measurements of alertness difficult.

The physiologic parameters demonstrate that an oral ills. dose of 40 mg of hydrocortisone given at 10 p.m. or 1–2 hours before the effective predetermined time does replicate the circadian rise and fall of cortisol, though at a slightly higher serum level than might occur with normal physiologic replacements. This is a situation where a person is initiating a work shift at midnight after being accustomed to day work. A morning rise in endogenous cortisol did occur on nights on which hydrocortisone was administered suggesting that even this dose was not sufficient to provide suppression. Adrenal suppression did not occur on the cosyntropin follow-up testing in an intervention that occurred on average once a month.

The most intriguing finding of the study is the subjective data. The physicians were able to discern that nights with drug were "good" nights to a high degree of significance. The first question any emergency physician asks another when relieving them after a night shift is, "How was it?" The question has more to do with coping with the physiological stress than the work load.

What are the risks of long term hydrocortisone? This study used only one treatment of hydrocortisone on single first nights and no physician took hydrocortisone more frequently than once a month. The long term effects of hydrocortisone treatment would not be seen in single episodic treatments such as this. Those attempting to reproduce this effect must be cautioned that the lack of effect on cosyntropin testing or adrenal suppression may not be reproduced if used more frequently.

Studies of this nature have certain inherent difficulties that will need to be overcome if future studies of a similar nature are to be done on a larger scale. Sleep ahead of time before shift work was not controlled in this project. Most physicians reported napping an hour or two prior to a first night shift—but reported having trouble doing so because they were still day entrained. Shift length was approximately the same but many EDs have 12 and 14-hour night shifts.

This study does not suggest that the use of hydrocortisone resolves the problems of night shift workers. Subjective improvement was sufficiently positive as to offer a glimmer of hope to a previously unexplored strategy.

That possibility may involve a variety of interventions to assist those in the transition zone of time period entrainment. The use of a vital hormone to replace a physiologic deficit may not apply only to night shift workers working a first night, but also to international travelers shifting multiple time zones.

Hydrocortisone, administered to night shift physicians on their first night after day entrainment, is an effective means of decreasing subjective symptoms of fatigue and stress. It is not clear whether it is possible to improve objective performance parameters by such an intervention.

Hydrocortisone is also an effective means of combating jet lag. A single 20 milligram tablet of hydrocortisone taken on arrival in London around, for example, 7 a.m. to 9 a.m. can trick your body clock which is telling you, "It's 2 a.m. central time in the United States, let's get some eye!" Best results are obtained if the hydrocortisone is administered at a precise time that replicates the normal human secretion of hydrocortisone at 7 a.m. in a traveler whose body is conditioned to a time zone greater than 4 hours away. The hydrocortisone should be administered at the precise time in the circadian rhythm that correlates to the number of time zones changed and have these changes compare to the former reference time zones.

The inventor has used it himself and offered it to friends, most of whom reported positive results. The inventor has used it for years when working the graveyard shift in the emergency room, as have some other of his colleagues who swear to its ability to ward off the feeling of an all-nighter. He has used it for international travel to reduce fatigue in jet lag for great benefit.

A dose of hydrocortisone acts according to the following: There is a circadian rise and fall in levels of cortisol, a corticosteroid, about every 24 hours. Blood levels of cortisol peak about 7 a.m. to 8 a.m. for a normal person who awakens at 7 a.m., at about 16 to 20 micrograms per deciliter. By noon, it declines to 10 to 15 micrograms, falling further by about 5 p.m. and reaching a low between 2–5 between midnight and 5 a.m.

If a 20 milligram tablet of hydrocortisone is taken in the morning upon landing in London after an overnight flight from the U.S.A. or a related time zone, it converts into cortisol, mimicking a level of 20 micrograms per deciliter in the blood in a traveler who would otherwise have an cortisol level of 2–5 micrograms. By immediately assisting in mobilizing sugars and other energy forms and breaking them down into energy, there is a boost and a heightened sense of wakefulness and activity level.

Attempts have been legion to mitigate the problems of jet lag—a condition in which the body's sense of time is so out of whack with the time zone upon landing that it produces myriad symptoms, including extreme fatigue, nausea, headaches, memory problems, attention deficit, appetite disturbances, depression, anxiety and clouded thinking. The precise timing of the administration of hydrocortisone overcomes these symptoms and assists in adjusting to time zone changes.

REFERENCES:
1. United State Department of Labor, Bureau of Labor Statistics: Workers on Flexible and Shift Schedule, Washington DC, US Government Printing Office, 1992.
2. Waeckerle, J. F. Circadian rhythm, shift work and emergency physicians. *Ann Emerg Med* 1994; 24:959–961
3. Skene D. J., Deacon S., Arendt J., Use of melatonin in circadian rhythm disorders and following phase shifts. Acta *Neurobiol Exp* (Warsz) 1996;56:359–62.
4. James M., Tremea M. O., Jones J. S., et al, Can Melatonin improve adaptation to night shift? *Am J Emerg Med* 1998;16:367–370.
5. Wright S. W., Lawrence L. M., Wrenn K. D., et al, Randomized clinical trial of melatonin after night-shift work: efficacy and neuropsychological effects. *Ann Emerg Med* 1998;32:334–40.
6. Mitler, M. M., Carskadon M. D., Czeisler C. A., et al: Catastrophes, sleep, and public policy: Consensus report. *Sleep* 1988; 11:100–109.
7. Mellor, E. F., Shift work and flextime: how prevalent are they? *Mon Labor Rev* 1986; November: 14–21.
8. Benedict F. G., Studies in body-temperature 1. Influence of the inversion of the daily routine, the temperature of night-workers. *Am J Physiolo.* 1904:145–169.
9. Knauth P., et al. Experimental Shift Work Studies of Permanent Night, and Rapidly Rotating, Shift Systems. *Int. Arch. Occup. Environ. Health* 1980:46:111–125.
10. Folkard S., Monk T. H., Lobban M. D., Short and long-term adjustment of circadian rhythms in "permanent" night nurses. *Ergonomics* 1978:21:785–99.
11. Harris, W., Fatigue, circadian rhythm, and truck accidents. In Mackie RR, ed. *Vigilance Theory, Operational Performance, and Physiological Correlates*, New York: Plenum, 1997:133–146.
12. Foret J., Lantin G., The sleep of train drivers: an example of the effects of irregular work schedules on sleep. In Colquhuon WP, *Aspects of human efficiency, diurnal rhythm and loss of sleep*. Cambridge: English Universities Press, 1972;273–282.
13. Toufexis A., Drowsy America, *Time Magazine*, 1990, Dec. 17: p78–85.
14. Czeisler C. A., Johnson M. P., Duffy J. F., et al, Exposure to bright light and darkness to treat physiological maladaptation to night work. *N Engl J Med* 1990;322:1253–1259.
15. Moore-Ede, M. C., Smelzer W. S. et al, Cortisol-mediated synchronization of circadian rhythm in urinary potassium excretion. *Am J Physiol* 1977;233:230–238.
16. Moore-Ede, M. C., Richardson, G. S., Medical Implications of Shift-Work. *Ann. Rev. Med* 1985; 36:607–617.
17. Dwyer B. J., Whitehead, D. C. et al, Surviving the 10-Year Ache: Emergency Practice Burnout. *Emergency Medicine Reports*, 1990 12:SS 1–8.
18. Aschoff J., Circadian rhythms within and outside their ranges of entrainment. In Assenmacher 1, Farner D S, *Environmental Endocrinology* New York: Springer-Verlag. 1978:172–181.
19. Keller K. L., Koenig, W. J., Management of stress and prevention of burnout in emergency physicians. *Ann Emerg Med* 1991:18;42–47.
20. Adams S. L., Roxe D. M., et al, Ambulatory blood pressure and Holter monitoring of emergency physician before, during, and after a night shift. *Acad Emerg Med* 1998;5:871–877.
21. Smith-Coggins R., Rosekind M. R., et al, Rotating shift-work schedule: can we enhance physician adaptation to night shifts. *Acad Emerg Med* 1997;4:951–961.
22. Michaels H. E., Night shift work. *Ann Emerg Med* 1984;13:201–202.
23. Bartle E. J., et al, The effects of acute sleep deprivation during residency training. *Surgery* 1988;104:311–6.
24. McNair, D. M., Lorr, M., Droppleman L. F., Profile of Mood States. EDITS/Educational and Industrial Testing Service, 1971–81.
25. Raff H., and Findling J. W. Evaluation of a new immunoradiometric (IRMA) assay for ACTH in normal subjects and patients with Cushing's syndrome. *Clin. Chem.* 1989;35:596–600.
26. Munck A., Buyre P. M., Holbrook N. J.: Physiological functions of glucocorticoids in stress and their relation to pharmacological actions. Endocrine Reviews 1984;5:25–44.
27. Whitcomb J. E., Finding J. W., Raff H., Hamsher K.: Randomized Trial of Oral Hydrocortisone and its Effect on Emergency Physicians during Night Duty.

Others may readily adapt the invention for use under various conditions of service by employing one or more of the novel features disclosed or equivalents thereof. All such which do not depart from the spirit of this disclosure are intended to be within its scope, which at present advised is best defined in the appended claims.

What is claimed is:

1. A method of decreasing fatigue in a human involved in a work shift or travel across several time zones comprising administering to the human an effective amount of hydrocortisone in association with said work shift and travel.

2. The method of claim 1 wherein the hydrocortisone is administered at a dosage in the range of 20–40 mg.

3. The method of claim 1 wherein the hydrocortisone is administered at a dosage of 20 mg.

4. The method of claim 1 wherein the hydrocortisone is administered at a dosage of 40 mg.

5. The method of claim 1 wherein the hydrocortisone is administered in the range of about 1–2 hours prior to a predetermined time.

6. The method of claim 5 wherein the human is initiating a work shift at midnight after being accommodated to day work.

7. The method of claim 1 wherein the hydrocortisone is administered in a single dose.

8. A method of reducing the fatigue of jet lag in a human involved in travel across several time zones comprising administering to said human an effective amount of hydrocortisone in association with said travel on arrival at a destination.

9. A method of reducing the fatigue of jet lag comprising administering to a human an effective amount of hydrocortisone on arrival at a destination wherein the hydrocortisone is administered at a precise time that replicates the normal human secretion of hydrocortisone at 7 a.m. in a traveler whose body is conditioned to a time zone greater than 4 hours away.

10. A method of reducing the fatigue of jet lag comprising administering to a human an effective amount of hydrocortisone at the precise time in a circadian rhythm that correlates to the number of time zones changed and how these changes compare to former reference time zones.

* * * * *

UNITED STATES PATENT AND TRADEMARK OFFICE
CERTIFICATE OF CORRECTION

PATENT NO. : 6,156,743  
DATED : December 5, 2000  
INVENTOR(S) : John E. Whitcomb Page 1 of 1

It is certified that error appears in the above-identified patent and that said Letters Patent is hereby corrected as shown below:

Column 5,
Line 62, replace "oral ills." with -- oral --.

Column 6,
Line 50, replace "some eye!" with -- some shut-eye!" --.

Signed and Sealed this

Sixteenth Day of October, 2001

Attest:

*Attesting Officer*

NICHOLAS P. GODICI
*Acting Director of the United States Patent and Trademark Office*